(12) United States Patent
Ishida et al.

(10) Patent No.: US 8,624,062 B2
(45) Date of Patent: Jan. 7, 2014

(54) METHOD FOR PRODUCING PHENYLACETAMIDE COMPOUND

(75) Inventors: Hajime Ishida, Saijo (JP); Masaji Hirota, Ibaraki (JP); Yoko Miyanaga, Ibaraki (JP); Yuya Mizushima, Misawa (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 209 days.

(21) Appl. No.: 13/147,823

(22) PCT Filed: Feb. 12, 2010

(86) PCT No.: PCT/JP2010/052486
§ 371 (c)(1),
(2), (4) Date: Aug. 4, 2011

(87) PCT Pub. No.: WO2010/093059
PCT Pub. Date: Aug. 19, 2010

(65) Prior Publication Data
US 2011/0295035 A1 Dec. 1, 2011

(30) Foreign Application Priority Data

Feb. 16, 2009 (JP) .................. 2009-032333
Jun. 11, 2009 (JP) .................. 2009-139899
Oct. 6, 2009 (JP) .................. 2009-232242

(51) Int. Cl.
C07C 233/05 (2006.01)
C07C 231/06 (2006.01)

(52) U.S. Cl.
USPC .......................... 564/170; 564/129

(58) Field of Classification Search
USPC .................................. 564/129, 170
See application file for complete search history.

(56) References Cited

U.S. PATENT DOCUMENTS 5,948,819 A    9/1999  Ohtsuka et al.
7,705,053 B2 * 4/2010  Koyano et al. ............... 514/617

FOREIGN PATENT DOCUMENTS

JP    09-095462 A    4/1997
JP    09-227487 A    9/1997
JP    2003-026640 A  1/2003
WO    9527693 A1     10/1995
WO    0210101 A1     2/2002

OTHER PUBLICATIONS

Khimiya Organ. Soedin. Azota, Perm, 24-32; 1981.*
Int'l Search Report issued Apr. 6, 2010 in Int'l Application No. PCT/JP2010/052486.

* cited by examiner

Primary Examiner — Shailendra Kumar
(74) Attorney, Agent, or Firm — Panitch Schwarze Belisario & Nadel LLP

(57) ABSTRACT

A method for producing a phenylacetamide compound represented by formula (1):

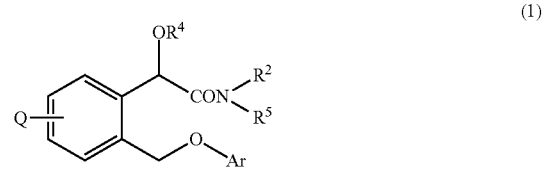

(1)

wherein Q represents a hydrogen atom or a halogen atom, $R^2$ represents a hydrogen atom or an alkyl group having 1 to 4 carbon atoms, $R^4$ represents an alkyl group having 1 to 4 carbon atoms, Ar represents an unsubstituted or substituted phenyl group, $R^5$ represents $R^4$ when $R^2$ is a hydrogen atom, and $R^5$ represents a hydrogen atom when $R^2$ is an alkyl group having 1 to 4 carbon atoms; including reacting a phenylacetamide compound represented by formula (2):

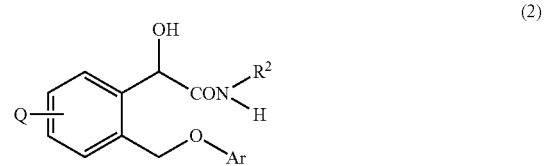

(2)

wherein Q, $R^2$ and Ar have the same meanings as defined above; with a dialkyl sulfate represented by formula (3):

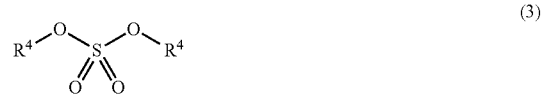

(3)

wherein $R^4$ has the same meaning as defined above;
in the presence of a base.

13 Claims, No Drawings

METHOD FOR PRODUCING PHENYLACETAMIDE COMPOUND

CROSS-REFERENCE TO RELATED APPLICATION

This application is a Section 371 of International Application No. PCT/JP2010/052486, filed Feb. 12, 2010, which was published in the Japanese language on Aug. 19, 2010, under International Publication No. WO 2010/093059 A1, and the disclosure of which is incorporated herein by reference.

TECHNICAL FIELD

The present invention relates to a method for producing a phenylacetamide compound.

BACKGROUND ART

WO 95/27693 discloses that a 2-substituted phenyl-N-alkylacetamide compound having an alkoxy group at the 2-position typified by 2-[2-(2,5-dimethylphenoxymethyl)phenyl]-2-methoxy-N-methylacetamide is useful as an agricultural fungicide, and also discloses, as a method for producing the compound; a method in which methyl 2-[2-(2,5-dimethylphenoxymethyl)phenyl]-2-hydroxyacetate is reacted with methyl iodide to obtain methyl 2-[2-(2,5-dimethylphenoxymethyl)phenyl]-2-methoxyacetate, and then the methyl 2-[2-(2,5-dimethylphenoxymethyl)phenyl]-2-methoxyacetate is reacted with methylamine to obtain 2-[2-(2,5-dimethylphenoxymethyl)phenyl]-2-methoxy-N-methylacetamide.

DISCLOSURE OF THE INVENTION

The present invention provides
[1] a method for producing a phenylacetamide compound represented by formula (1):

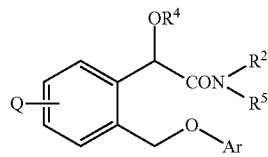

(1)

wherein Q represents a hydrogen atom or a halogen atom, $R^2$ represents a hydrogen atom or an alkyl group having 1 to 4 carbon atoms, $R^4$ represents an alkyl group having 1 to 4 carbon atoms, Ar represents an unsubstituted or substituted phenyl group, $R^5$ represents $R^4$ when $R^2$ is a hydrogen atom, and $R^5$ represents a hydrogen atom when $R^2$ is an alkyl group having 1 to 4 carbon atoms; comprising reacting a phenylacetamide compound represented by formula (2):

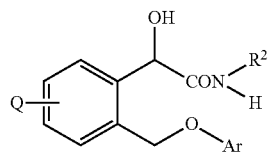

(2)

wherein Q, $R^2$ and Ar have the same meanings as defined above; with a dialkyl sulfate represented by formula (3):

(3)

wherein $R^4$ has the same meaning as defined above;
in the presence of a base;
[2] the production method according to [1], wherein $R^2$ is a hydrogen atom;
[3] the production method according to [1] or [2], wherein Ar is a 2,5-dimethylphenyl group or a 2-methylphenyl group;
[4] the production method according to [1] or [2], wherein Ar is a 2,5-dimethylphenyl group;
[5] the production method according to any one of [1] to [4], wherein $R^4$ is a methyl group;
[6] the production method according to any one of [1] to [5], wherein the base is an alkali metal hydroxide;
[7] the production method according to one of [1] to [6], wherein the phenylacetamide compound represented by formula (2) is a phenylacetamide compound obtained by reacting an acetic acid ester compound represented by formula (4):

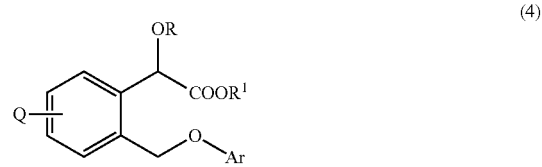

(4)

wherein Q represents a hydrogen atom or a halogen atom, Ar represents an unsubstituted or substituted phenyl group, and $R^1$ represents an alkyl group having 1 to 4 carbon atoms; with an amine compound represented by formula (5):

$$R^2-NH_2 \quad (5)$$

wherein $R^2$ represents a hydrogen atom or an alkyl group having 1 to 4 carbon atoms;
[8] the production method according to [7], wherein the reaction of the acetic acid ester compound represented by formula (4) with the amine compound represented by formula (5) is carried out in the presence of an alcohol solvent having 1 to 4 carbon atoms;
[9] the production method according to [7] or [8], wherein the acetic acid ester compound represented by formula (4) is an acetic acid ester compound obtained by reacting a mandelonitrile compound represented by formula (6):

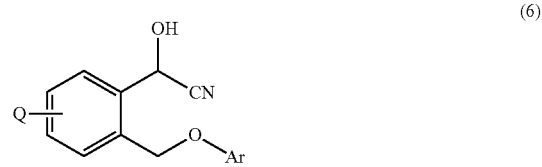

(6)

wherein Q represents a hydrogen atom or a halogen atom, and Ar represents an unsubstituted or substituted phenyl group;
with an alcohol compound represented by formula (7):

(7)

wherein R¹ represents an alkyl group having 1 to 4 carbon atoms; and an acid, and then reacting the resulting product with water;

[10] the production method according to [2], wherein the phenylacetamide compound represented by formula (2) is a phenylacetamide compound obtained by reacting the mandelonitrile compound represented by formula (6):

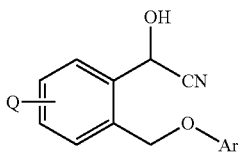
(6)

wherein Q represents a hydrogen atom or a halogen atom, and Ar represents an unsubstituted or substituted phenyl group; with 0.1 to 1 mol of hydrogen chloride and 1 to 4 mol of water, based on 1 mol of the mandelonitrile compound;

[11] the production method according to [10], wherein the reaction of the mandelonitrile compound represented by formula (6) with hydrogen chloride and water is carried out in the presence of an aromatic hydrocarbon solvent;

[12] a method for producing a phenylacetamide compound represented by formula (8):

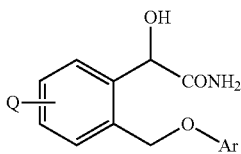
(8)

wherein Q represents a hydrogen atom or a halogen atom, and Ar represents an unsubstituted or substituted phenyl group; comprising reacting a mandelonitrile compound represented by formula (6):

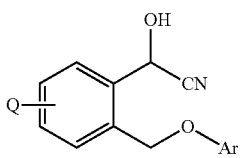
(6)

wherein Q and Ar have the same meanings as defined above; with 0.1 to 1 mol of hydrogen chloride and 1 to 4 mol of water, based on 1 mol of the mandelonitrile compound;

[13] the production method according to [12], wherein the reaction of the mandelonitrile compound represented by formula (6) with hydrogen chloride and water is carried out in the presence of an aromatic hydrocarbon solvent; and the like.

BEST MODE FOR CARRYING OUT THE INVENTION

In the phenylacetamide compound represented by formula (2) (hereinafter abbreviated to an acetamide compound (2)), Q represents a hydrogen atom or a halogen atom.

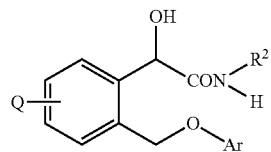
(2)

Examples of the halogen atom include a fluorine atom, a chlorine atom, a bromine atom and an iodine atom. Q is preferably a hydrogen atom.

R² in formula (2) represents a hydrogen atom or an alkyl group having 1 to 4 carbon atoms. Examples of the alkyl group having 1 to 4 carbon atoms include a methyl group, an ethyl group, a propyl group, an isopropyl group, a butyl group, a sec-butyl group, an isobutyl group and a tert-butyl group, and a methyl group is preferred. R² is preferably a hydrogen atom.

Ar represents an unsubstituted or substituted phenyl group. Examples of the substituent include alkyl groups having 1 to 4 carbon atoms, such as a methyl group, an ethyl group, a propyl group, an isopropyl group, a butyl group, an isobutyl group and a tert-butyl group; and halogen atoms such as a fluorine atom and a chlorine atom. There is no particular limitation on the number of substituents, and the number of substituents is preferably 1 to 3, more preferably 1 or 2, and particularly preferably 2.

Examples of the substituted phenyl group include a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2,4,6-trimethylphenyl group, a 2-ethylphenyl group, a 3-ethylphenyl group, a 4-ethylphenyl group, a 2,3-diethylphenyl group, a 2,4-diethylphenyl group, a 2,5-diethylphenyl group, a 2,6-diethylphenyl group, a 3,5-diethylphenyl group, a 2,4,6-triethylphenyl group, a 2-propylphenyl group, a 3-propylphenyl group, a 4-propylphenyl group, a 2,4-dipropylphenyl group, a 2,5-dipropylphenyl group, a 2,6-dipropylphenyl group, a 2,4,6-tripropylphenyl group, a 2-isopropylphenyl group, a 3-isopropylphenyl group, a 4-isopropylphenyl group, a 2,4-isopropylphenyl group, a 2,5-diisopropylphenyl group, a 2,6-diisopropylphenyl group, a 2,4,6-triisopropylphenyl group, a 2-butylphenyl group, a 3-butylphenyl group, a 4-butylphenyl group, a 2,4-dibutylphenyl group, a 2,5-dibutylphenyl group, a 2,6-dibutylphenyl group, a 2,4,6-tributylphenyl group, a 2-isobutylphenyl group, a 3-isobutylphenyl group, a 4-isobutylphenyl group, a 2,4-diisobutylphenyl group, a 2,5-diisobutylphenyl group, a 2,6-diisobutylphenyl group, a 2,4,6-triisobutylphenyl group, a 2-(tert-butyl)phenyl group, a 3-(tert-butyl)phenyl group, a 4-(tert-butyl)phenyl group, a 2,5-di-(tert-butyl)phenyl group, a 2,4-di-(tert-butyl)phenyl group, a 2,6-di-(tert-butyl)phenyl group, a 2,4,6-tri-(tert-butyl)phenyl group, a 2-fluorophenyl group, a 4-fluorophenyl group, a 2,4-difluorophenyl group, a 2,4,6-trifluorophenyl group, a pentafluorophenyl group, a 2-chlorophenyl group, a 4-chlorophenyl group, a 2,4-dichlorophenyl group, a 2,4,6-trichlorophenyl group, and a pentachlorophenyl group. Among these groups, a 2,5-dimethylphenyl group and a 2-methylphenyl group are preferred, and a 2,5-dimethylphenyl group is more preferred.

Examples of the acetamide compound (2) include 2-hydroxyacetamide compounds such as
2-[2-(phenoxymethyl)phenyl]-2-hydroxyacetamide,
2-[2-(2-methylphenoxymethyl)phenyl]-2-hydroxyacetamide, 2-[2-(3-methylphenoxymethyl)phenyl]-2-hydroxyacetamide,
2-[2-(4-methylphenoxymethyl)phenyl]-2-hydroxyacetamide,
2-[2-(2-ethylphenoxymethyl)phenyl]-2-hydroxyacetamide,
2-[2-(4-ethylphenoxymethyl)phenyl]-2-hydroxyacetamide,
2-[2-(2-isopropylphenoxymethyl)phenyl]-2-hydroxyacetamide,
2-[2-(4-isopropylphenoxymethyl)phenyl]-2-hydroxyacetamide,
2-[2-(2-tert-butylphenoxymethyl)phenyl]-2-hydroxyacetamide,
2-[2-(4-tert-butylphenoxymethyl)phenyl]-2-hydroxyacetamide,
2-[2-(2,4-dimethylphenoxymethyl)phenyl]-2-hydroxyacetamide,
2-[2-(2,5-dimethylphenoxymethyl)phenyl]-2-hydroxyacetamide,
2-[2-(2,6-dimethylphenoxymethyl)phenyl]-2-hydroxyacetamide,
2-[2-(3,5-dimethylphenoxymethyl)phenyl]-2-hydroxyacetamide,
2-[2-(2,4-diethylphenoxymethyl)phenyl]-2-hydroxyacetamide,
2-[2-(2,5-diethylphenoxymethyl)phenyl]-2-hydroxyacetamide,
2-[2-(2,6-diethylphenoxymethyl)phenyl]-2-hydroxyacetamide,
2-[2-(2,5-diisopropylphenoxymethyl)phenyl]-2-hydroxyacetamide,
2-[2-(2,6-diisopropylphenoxymethyl)phenyl]-2-hydroxyacetamide,
2-[2-(2,4,5-trimethylphenoxymethyl)phenyl]-2-hydroxyacetamide,
2-[2-(2,4,6-trimethylphenoxymethyl)phenyl]-2-hydroxyacetamide,
2-[2-(3,4,5-trimethylphenoxymethyl)phenyl]-2-hydroxyacetamide,
2-[2-(2,5-dimethylphenoxymethyl)-3-chlorophenyl]-2-hydroxyacetamide,
2-[2-(2-methylphenoxymethyl)-3-chlorophenyl]-2-hydroxyacetamide,
2-[2-(2,5-dimethylphenoxymethyl)-4-chlorophenyl]-2-hydroxyacetamide,
2-[2-(2-methylphenoxymethyl)-4-chlorophenyl]-2-hydroxyacetamide,
2-[2-(2,5-dimethylphenoxymethyl)-5-chlorophenyl]-2-hydroxyacetamide,
2-[2-(2-methylphenoxymethyl)-5-chlorophenyl]-2-hydroxyacetamide,
2-[2-(2,5-dimethylphenoxymethyl)-6-chlorophenyl]-2-hydroxyacetamide,
2-[2-(2-methylphenoxymethyl)-6-chlorophenyl]-2-hydroxyacetamide,
2-[2-(2,5-diethylphenoxymethyl)-4-chlorophenyl]-2-hydroxyacetamide,
2-[2-(2-ethylphenoxymethyl)-4-chlorophenyl]-2-hydroxyacetamide,
2-[2-(2,5-diisopropylphenoxymethyl)-4-chlorophenyl]-2-hydroxyacetamide, and
2-[2-(2-isopropylphenoxymethyl)-4-chlorophenyl]-2-hydroxyacetamide;
2-hydroxy-N-methylacetamide compounds such as
2-[2-(phenoxymethyl)phenyl]-2-hydroxy-N-methylacetamide,
2-[2-(2-methylphenoxymethyl)phenyl]-2-hydroxy-N-methylacetamide,
2-[2-(3-methylphenoxymethyl)phenyl]-2-hydroxy-N-methylacetamide,
2-[2-(4-methylphenoxymethyl)phenyl]-2-hydroxy-N-methylacetamide,
2-[2-(2-ethylphenoxymethyl)phenyl]-2-hydroxy-N-methylacetamide,
2-[2-(4-ethylphenoxymethyl)phenyl]-2-hydroxy-N-methylacetamide,
2-[2-(2-isopropylphenoxymethyl)phenyl]-2-hydroxy-N-methylacetamide,
2-[2-(4-isopropylphenoxymethyl)phenyl]-2-hydroxy-N-methylacetamide,
2-[2-(2-tert-butylphenoxymethyl)phenyl]-2-hydroxy-N-methylacetamide,
2-[2-(4-tert-butylphenoxymethyl)phenyl]-2-hydroxy-N-methylacetamide,
2-[2-(2,4-dimethylphenoxymethyl)phenyl]-2-hydroxy-N-methylacetamide,
2-[2-(2,5-dimethylphenoxymethyl)phenyl]-2-hydroxy-N-methylacetamide,
2-[2-(2,6-dimethylphenoxymethyl)phenyl]-2-hydroxy-N-methylacetamide,
2-[2-(3,5-dimethylphenoxymethyl)phenyl]-2-hydroxy-N-methylacetamide,
2-[2-(2,4-diethylphenoxymethyl)phenyl]-2-hydroxy-N-methylacetamide,
2-[2-(2,5-diethylphenoxymethyl)phenyl]-2-hydroxy-N-methylacetamide,
2-[2-(2,6-diethylphenoxymethyl)phenyl]-2-hydroxy-N-methylacetamide,
2-[2-(2,5-diisopropylphenoxymethyl)phenyl]-2-hydroxy-N-methylacetamide,
2-[2-(2,6-diisopropylphenoxymethyl)phenyl]-2-hydroxy-N-methylacetamide,
2-[2-(2,4,5-trimethylphenoxymethyl)phenyl]-2-hydroxy-N-methylacetamide,
2-[2-(2,4,6-trimethylphenoxymethyl)phenyl]-2-hydroxy-N-methylacetamide,
2-[2-(3,4,5-trimethylphenoxymethyl)phenyl]-2-hydroxy-N-methylacetamide,
2-[2-(2,5-dimethylphenoxymethyl)-3-chlorophenyl]-2-hydroxy-N-methylacetamide,
2-[2-(2-methylphenoxymethyl)-3-chlorophenyl]-2-hydroxy-N-methylacetamide,
2-[2-(2,5-dimethylphenoxymethyl)-4-chlorophenyl]-2-hydroxy-N-methylacetamide,
2-[2-(2-methylphenoxymethyl)-4-chlorophenyl]-2-hydroxy-N-methylacetamide,
2-[2-(2,5-dimethylphenoxymethyl)-5-chlorophenyl]-2-hydroxy-N-methylacetamide,
2-[2-(2-methylphenoxymethyl)-5-chlorophenyl]-2-hydroxy-N-methylacetamide,
2-[2-(2,5-dimethylphenoxymethyl)-6-chlorophenyl]-2-hydroxy-N-methylacetamide,
2-[2-(2-methylphenoxymethyl)-6-chlorophenyl]-2-hydroxy-N-methylacetamide,
2-[2-(2,5-diethylphenoxymethyl)-4-chlorophenyl]-2-hydroxy-N-methylacetamide,
2-[2-(2-ethylphenoxymethyl)-4-chlorophenyl]-2-hydroxy-N-meth ylacetamide,
2-[2-(2,5-diisopropylphenoxymethyl)-4-chlorophenyl]-2-hydroxy-N-methylacetamide, and
2-[2-(2-isopropylphenoxymethyl)-4-chlorophenyl]-2-hydroxy-N-methylacetamide; and
compounds in which N-methyl in the above 2-hydroxy-N-methylacetamide compounds is replaced by N-ethyl, N-propyl, N-isopropyl or N-butyl.

Among these compounds, a 2-hydroxyacetamide compound and a 2-hydroxy-N-methylacetamide compound are preferred.

In the dialkyl sulfate represented by formula (3) (hereinafter abbreviated to a dialkyl sulfate (3)), $R^4$ represents an alkyl group having 1 to 4 carbon atoms.

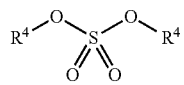

(3)

Examples of the alkyl group having 1 to 4 carbon atoms include a methyl group, an ethyl group, a propyl group, an isopropyl group, a butyl group, a sec-butyl group, an isobutyl group and a tert-butyl group, and a methyl group is preferred.

Examples of the dialkyl sulfate (3) include dialkyl sulfates having a linear alkyl group, such as dimethyl sulfate, diethyl sulfate, dipropyl sulfate and dibutyl sulfate; and dialkyl sulfates having a branched alkyl group, such as diisopropyl sulfate and diisobutyl sulfate, and dialkyl sulfates having a linear alkyl group are preferred, and dimethyl sulfate is more preferred.

As such dialkyl sulfates (3), commercially available dialkyl sulfates or those produced by a known method may be used.

The amount of the dialkyl sulfate (3) used is usually from 1 to 20 mol, and preferably from 1 to 10 mol, based on 1 mol of the acetamide compound (2).

The reaction of the acetamide compound (2) with the dialkyl sulfate (3) is carried out in the presence of a base. Examples of the base include alkali metal hydroxides such as sodium hydroxide and potassium hydroxide; and alkaline earth metal hydroxides such as barium hydroxide and calcium hydroxide, and alkali metal hydroxides are preferred, and sodium hydroxide is more preferably.

The amount of the base used is usually from 2 to 50 mol, and preferably from 2 to 20 mol, based on 1 mol of the acetamide compound (2).

The reaction of the acetamide compound (2) with the dialkyl sulfate (3) is usually carried out in the presence of a solvent inert in the reaction. Examples of the solvent include alcohol solvents such as methanol and ethanol; aromatic hydrocarbon solvents such as toluene and xylene; ether solvents such as diethyl ether and tetrahydrofuran; and water. These solvents may be used alone, two or more kinds of solvents may be used in combination. Among these solvents, aromatic hydrocarbon solvents are preferred, and toluene or xylene is more preferred. There is no particular limitation on the amount of the solvents used, and it is preferably from 0.5 to 100 parts by weight, and more preferably from 1 to 20 parts by weight, based on 1 part by weight of the acetamide compound (2).

The reaction of the acetamide compound (2) with the dialkyl sulfate (3) is carried out by mixing the acetamide compound (2), the dialkyl sulfate (3) and the base, and there is no particular limitation on the mixing order of these components. For example, the dialkyl sulfate (3) and the base may be simultaneously added to the acetamide compound (2) adjusted to reaction temperature, or the base may be added to the acetamide compound (2) adjusted to reaction temperature and then the dialkyl sulfate (3) may be added. Among these, it is preferred that the base is added to the acetamide compound (2) adjusted to reaction temperature, and then the dialkyl sulfate (3) may be added. There is no particular limitation on the time of the base and the dialkyl sulfate (3) added.

The reaction temperature is usually from 0 to 70° C., and preferably from 10 to 50° C. The reaction time depends on the reaction temperature, and is usually from 0.5 to 20 hours, and preferably from 1 to 10 hours.

The progress of the reaction can be recognized by general analytical means such as high-performance liquid chromatography and gas chromatography.

After completion of the reaction, for example, the obtained reaction mixture may be washed with water or an aqueous acid solution such as diluted hydrochloric acid, and then concentrated to obtain a phenylacetamide compound represented by formula (1) (hereinafter abbreviated to a phenylacetamide compound (1)):

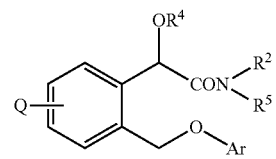

(1)

wherein Q, $R^2$, $R^4$ and Ar have the same meanings as defined above; $R^5$ represents $R^4$ when $R^2$ is a hydrogen atom and $R^5$ represents a hydrogen atom when $R^2$ is an alkyl group having 1 to 4 carbon atoms. The phenylacetamide compound (1) thus obtained may be further purified by general purification means such as column chromatography.

When the acetamide compound (2) wherein $R^2$ is an alkyl group having 1 to 4 carbon atoms is used, the phenylacetamide compound (1) is obtained wherein a hydroxyl group at the 2-position is alkylated and a nitrogen atom on the amide moiety is not alkylated. When the acetamide compound (2) wherein $R^2$ is a hydrogen atom is used, the phenylacetamide compound (1) is obtained wherein a hydroxyl group at the 2-position is alkylated and a nitrogen atom on the amide moiety is also monoalkylated. The method of the present invention is advantageous because the phenylacetamide compound (1) wherein a hydroxyl group at the 2-position is alkylated and a nitrogen atom on the amide moiety is also monoalkylated is obtained in one step when the acetamide compound (2) wherein $R^2$ is a hydrogen atom is used. Also, the phenylacetamide compound wherein a nitrogen atom on the amide moiety is dialkylated is scarcely generated as a by-product, when the acetamide compound (2) wherein $R^2$ is a hydrogen atom is used. Furthermore, a phenylacetamide compound wherein a nitrogen atom on the amide moiety is alkylated is scarcely generated as a by-product, even when the acetamide compound (2) wherein $R^2$ is an alkyl group having 1 to 4 carbon atoms is used. Accordingly, the objective phenylacetamide compound (1) can be obtained in good yield. Also, the phenylacetamide compound (1) having good purity can be easily obtained because of less by-products.

Examples of the phenylacetamide compound (1) thus obtained include

2-[2-(phenoxymethyl)phenyl]-2-methoxy-N-methylacetamide,

2-[2-(2-methylphenoxymethyl)phenyl]-2-methoxy-N-methylacetamide,

2-[2-(3-methylphenoxymethyl)phenyl]-2-methoxy-N-methylacetamide,

2-[2-(4-methylphenoxymethyl)phenyl]-2-methoxy-N-methylacetamide,

2-[2-(2-ethylphenoxymethyl)phenyl]-2-methoxy-N-methylacetamide,
2-[2-(4-ethylphenoxymethyl)phenyl]-2-methoxy-N-methylacetamide,
2-[2-(2-isopropylphenoxymethyl)phenyl]-2-methoxy-N-methylacetamide,
2-[2-(4-isopropylphenoxymethyl)phenyl]-2-methoxy-N-methylacetamide,
2-[2-(2-tert-butylphenoxymethyl)phenyl]-2-methoxy-N-methylacetamide,
2-[2-(4-tert-butylphenoxymethyl)phenyl]-2-methoxy-N-methylacetamide,
2-[2-(2,4-dimethylphenoxymethyl)phenyl]-2-methoxy-N-methylacetamide,
2-[2-(2,5-dimethylphenoxymethyl)phenyl]-2-methoxy-N-methylacetamide,
2-[2-(2,6-dimethylphenoxymethyl)phenyl]-2-methoxy-N-methylacetamide,
2-[2-(3,5-dimethylphenoxymethyl)phenyl]-2-methoxy-N-methylacetamide,
2-[2-(2,4-diethylphenoxymethyl)phenyl]-2-methoxy-N-methylacetamide,
2-[2-(2,5-diethylphenoxymethyl)phenyl]-2-methoxy-N-methylacetamide,
2-[2-(2,6-diethylphenoxymethyl)phenyl]-2-methoxy-N-methylacetamide,
2-[2-(2,5-diisopropylphenoxymethyl)phenyl]-2-methoxy-N-methylacetamide,
2-[2-(2,6-diisopropylphenoxymethyl)phenyl]-2-methoxy-N-methylacetamide,
2-[2-(2,4,5-trimethylphenoxymethyl)phenyl]-2-methoxy-N-methylacetamide,
2-[2-(2,4,6-trimethylphenoxymethyl)phenyl]-2-methoxy-N-methylacetamide,
2-[2-(3,4,5-trimethylphenoxymethyl)phenyl]-2-methoxy-N-methylacetamide,
2-[2-(2,5-dimethylphenoxymethyl)-3-chlorophenyl]-2-methoxy-N-methylacetamide,
2-[2-(2-methylphenoxymethyl)-3-chlorophenyl]-2-methoxy-N-methylacetamide,
2-[2-(2,5-dimethylphenoxymethyl)-4-chlorophenyl]-2-methoxy-N-methylacetamide,
2-[2-(2-methylphenoxymethyl)-4-chlorophenyl]-2-methoxy-N-methylacetamide,
2-[2-(2,5-dimethylphenoxymethyl)-5-chlorophenyl]-2-methoxy-N-methylacetamide,
2-[2-(2-methylphenoxymethyl)-5-chlorophenyl]-2-methoxy-N-methylacetamide,
2-[2-(2,5-dimethylphenoxymethyl)-6-chlorophenyl]-2-methoxy-N-methylacetamide,
2-[2-(2-methylphenoxymethyl)-6-chlorophenyl]-2-methoxy-N-methylacetamide,
2-[2-(2,5-diethylphenoxymethyl)-4-chlorophenyl]-2-methoxy-N-methylacetamide,
2-[2-(2-ethylphenoxymethyl)-4-chlorophenyl]-2-methoxy-N-methylacetamide,
2-[2-(2,5-diisopropylphenoxymethyl)-4-chlorophenyl]-2-methoxy-N-methylacetamide,
2-[2-(2-isopropylphenoxymethyl)-4-chlorophenyl]-2-methoxy-N-methylacetamide,
2-[2-(2-methylphenoxymethyl)phenyl]-2-ethoxy-N-ethylacetamide,
2-[2-(2,5-dimethylphenoxymethyl)phenyl]-2-ethoxy-N-ethylacetamide,
2-[2-(2-methylphenoxymethyl)phenyl]-2-propoxy-N-propylacetamide,
2-[2-(2,5-dimethylphenoxymethyl)phenyl]-2-propoxy-N-propylacetamide,
2-[2-(2-methylphenoxymethyl)phenyl]-2-butoxy-N-butylacetamide, and
2-[2-(2,5-dimethylphenoxymethyl)phenyl]-2-butoxy-N-butylacetamide.

Among them,
2-[2-(2-methylphenoxymethyl)phenyl]-2-methoxy-N-methylacetamide and
2-[2-(2,5-dimethylphenoxymethyl)phenyl]-2-hydroxy-N-methylacetamide are preferred, and
2-[2-(2,5-dimethylphenoxymethyl)phenyl]-2-methoxy-N-methylacetamide is more preferred.

The acetamide compound (2) can be produced by reacting an acetic acid ester compound represented by formula (4) (hereinafter abbreviated to an acetic acid ester compound (4)):

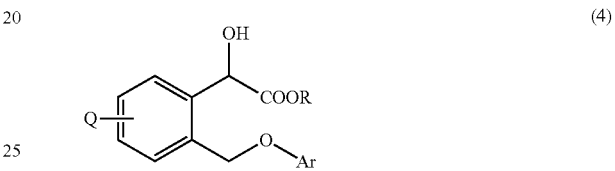

(4)

wherein Q and Ar have the same meanings as defined above, and $R^1$ represents an alkyl group having 1 to 4 carbon atoms; with an amine compound represented by formula (5) (hereinafter abbreviated to an amine compound (5)):

$R^2$—$NH_2$ (5)

wherein $R^2$ has the same meaning as defined above.

Examples of the acetic acid ester compound (4) include methyl 2-hydroxyacetate compounds such as methyl 2-[2-(phenoxymethyl)phenyl]-2-hydroxyacetate,
methyl 2-[2-(2-methylphenoxymethyl)phenyl]-2-hydroxyacetate,
methyl 2-[2-(3-methylphenoxymethyl)phenyl]-2-hydroxyacetate,
methyl 2-[2-(4-methylphenoxymethyl)phenyl]-2-hydroxyacetate,
methyl 2-[2-(2-ethylphenoxymethyl)phenyl]-2-hydroxyacetate,
methyl 2-[2-(4-ethylphenoxymethyl)phenyl]-2-hydroxyacetate,
methyl 2-[2-(2-isopropylphenoxymethyl)phenyl]-2-hydroxyacetate,
methyl 2-[2-(4-isopropylphenoxymethyl)phenyl]-2-hydroxyacetate,
methyl 2-[2-(2-tert-butylphenoxymethyl)phenyl]-2-hydroxyacetate,
methyl 2-[2-(4-tert-butylphenoxymethyl)phenyl]-2-hydroxyacetate,
methyl 2-[2-(2,4-dimethylphenoxymethyl)phenyl]-2-hydroxyacetate,
methyl 2-[2-(2,5-dimethylphenoxymethyl)phenyl]-2-hydroxyacetate,
methyl 2-[2-(2,6-dimethylphenoxymethyl)phenyl]-2-hydroxyacetate,
methyl 2-[2-(3,5-dimethylphenoxymethyl)phenyl]-2-hydroxyacetate,
methyl 2-[2-(2,4-diethylphenoxymethyl)phenyl]-2-hydroxyacetate,
methyl 2-[2-(2,5-diethylphenoxymethyl)phenyl]-2-hydroxyacetate, methyl 2-[2-(2,6-diethylphenoxymethyl)phenyl]-2-hydroxyacetate,
methyl 2-[2-(2,5-diisopropylphenoxymethyl)phenyl]-2-hydroxyacetate,
methyl 2-[2-(2,6-diisopropylphenoxymethyl)phenyl]-2-hydroxyacetate,
methyl 2-[2-(2,4,5-trimethylphenoxymethyl)phenyl]-2-hydroxyacetate,
methyl 2-[2-(2,4,6-trimethylphenoxymethyl)phenyl]-2-hydroxyacetate,
methyl 2-[2-(3,4,5-trimethylphenoxymethyl)phenyl]-2-hydroxyacetate,
methyl 2-[2-(2,5-dimethylphenoxymethyl)-3-chlorophenyl]-2-hydroxyacetate,
methyl 2-[2-(2-methylphenoxymethyl)-3-chlorophenyl]-2-hydroxyacetate,
methyl 2-[2-(2,5-dimethylphenoxymethyl)-4-chlorophenyl]-2-hydroxyacetate,
methyl 2-[2-(2-methylphenoxymethyl)-4-chlorophenyl]-2-hydroxyacetate,
methyl 2-[2-(2,5-dimethylphenoxymethyl)-5-chlorophenyl]-2-hydroxyacetate,
methyl 2-[2-(2-methylphenoxymethyl)-5-chlorophenyl]-2-hydroxyacetate,
methyl 2-[2-(2,5-dimethylphenoxymethyl)-6-chlorophenyl]-2-hydroxyacetate,
methyl 2-[2-(2-methylphenoxymethyl)-6-chlorophenyl]-2-hydroxyacetate,
methyl 2-[2-(2,5-diethylphenoxymethyl)-4-chlorophenyl]-2-hydroxyacetate,
methyl 2-[2-(2-ethylphenoxymethyl)-4-chlorophenyl]-2-hydroxyacetate
methyl 2-[2-(2,5-diisopropylphenoxymethyl)-4-chlorophenyl]-2-hydroxyacetate, and
methyl 2-[2-(2-isopropylphenoxymethyl)-4-chlorophenyl]-2-hydroxyacetate;
ethyl 2-hydroxyacetate compounds such as ethyl 2-[2-(2-methylphenoxymethyl)phenyl]-2-hydroxyacetate, and
ethyl 2-[2-(2,5-dimethylphenoxymethyl)phenyl]-2-hydroxyacetate;
propyl 2-hydroxyacetate compounds such as propyl 2-[2-(2-methylphenoxymethyl)phenyl]-2-hydroxyacetate, and
propyl 2-[2-(2,5-dimethylphenoxymethyl)phenyl]-2-hydroxyacetate;
isopropyl 2-hydroxyacetate compounds such as isopropyl 2-[2-(2-methylphenoxymethyl)phenyl]-2-hydroxyacetate, and
isopropyl 2-[2-(2,5-dimethylphenoxymethyl)phenyl]-2-hydroxyacetate;
butyl 2-hydroxyacetate compounds such as butyl 2-[2-(2-methylphenoxymethyl)phenyl]-2-hydroxyacetate, and
butyl 2-[2-(2,5-dimethylphenoxymethyl)phenyl]-2-hydroxyacetate;
isobutyl 2-hydroxyacetate compounds such as isobutyl 2-[2-(2-methylphenoxymethyl)phenyl]-2-hydroxyacetate;
tert-butyl 2-hydroxyacetate compounds such as tert-butyl 2-[2-(2-methylphenoxymethyl)phenyl]-2-hydroxyacetate, and
tert-butyl 2-[2-(2,5-dimethylphenoxymethyl)phenyl]-2-hydroxyacetate;
isobutyl 2-hydroxyacetate compounds such as isobutyl 2-[2-(2,5-dimethylphenoxymethyl)phenyl]-2-hydroxyacetate;
and the like. Among these compounds, methyl 2-[2-(2-methylphenoxymethyl)phenyl]-2-hydroxyacetate and methyl 2-[2-(2,5-dimethylphenoxymethyl)phenyl]-2-hydroxyacetate are preferred, and methyl 2-[2-(2,5-dimethylphenoxymethyl)phenyl]-2-hydroxyacetate is more preferred.

Examples of the amine compound (5) include ammonia and monoalkylamines such as methylamine, ethylamine, propylamine, isopropylamine, butylamine, isobutylamine and tert-butylamine, and methylamine is preferred.

As such amine compound (5), commercially available amine compounds or those produced by a known method may be used.

The amount of the amine compound (5) used is usually from 1 to 10 mol, and preferably from 1 to 6 mol, based on 1 mol of the acetic acid ester compound (4).

The reaction of the acetic acid ester compound (4) with the amine compound (5) is usually carried out in the presence of a solvent inert in the reaction. Examples of the solvent include alcohol solvents having 1 to 4 carbon atoms, such as methanol and ethanol; aromatic hydrocarbon solvents such as toluene and xylene; ether solvents such as diethyl ether and tetrahydrofuran; and water. These solvents may be used alone, or two or more kinds of solvents may be used in combination. Among these solvents, aromatic hydrocarbon solvents, alcohol solvents having 1 to 4 carbon atoms and mixed solvents thereof are preferred, and alcohol solvents having 1 to 4 carbon atoms and mixed solvents of alcohol solvents having 1 to 4 carbon atoms with aromatic hydrocarbon solvents are more preferred. There is no particular limitation on the amount of the solvent used, and it is usually from 0.5 to 100 parts by weight, and preferably from 1 to 10 parts by weight, based on 1 part by weight of the acetic acid ester compound (4).

The reaction temperature is usually from 0 to 100° C., and preferably from 20 to 60° C. The reaction time depends on the reaction temperature, and is usually from 0.5 to 100 hours, and preferably from 1 to 50 hours. The progress of the reaction can be recognized by general analytical methods such as high-performance liquid chromatography and gas chromatography.

The reaction of the acetic acid ester compound (4) with the amine compound (5) is usually carried out by mixing both compounds. There is no particular limitation on the mixing order and, for example, there is exemplified a method in which the amine compound (5) is usually added to the acetic acid ester compound (4) over 0.5 to 100 hours, and preferably over 1 to 50 hours.

After completion of the reaction, the obtained reaction mixture contains the acetamide compound (2). The reaction mixture may be used in the above reaction of the acetamide compound (2) with the dialkyl sulfate (3) directly or after washing. Alternatively, the acetamide compound (2) may be separated from the reaction mixture by concentration, crystallization or the like, and the acetamide compound (2) thus separated may be used in the above reaction of the acetamide compound (2) with the dialkyl sulfate (3). The acetamide compound (2) thus separated may be further purified by general purification means such as column chromatography.

The acetic acid ester compound (4) can be produced by reacting a mandelonitrile compound represented by formula (6) (hereinafter abbreviated to a mandelonitrile compound (6)):

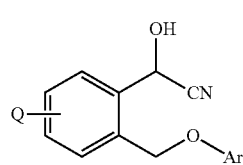

(6)

wherein Q and Ar have the same meanings as defined above; with an alcohol compound represented by formula (7) (hereinafter abbreviated to an alcohol compound (7)):

(7)

wherein R¹ has the same meaning defined above; and an acid, and then reacting the obtained product with water.

Examples of the mandelonitrile compound (6) include 2-(phenoxymethyl)mandelonitrile,
2-(2-methylphenoxymethyl)mandelonitrile,
2-(3-methylphenoxymethyl)mandelonitrile,
2-(4-methylphenoxymethyl)mandelonitrile,
2-(2-ethylphenoxymethyl)mandelonitrile,
2-(4-ethylphenoxymethyl)mandelonitrile,
2-(2-isopropylphenoxymethyl)mandelonitrile,
2-(4-isopropylphenoxymethyl)mandelonitrile,
2-(2-tert-butylphenoxymethyl)mandelonitrile,
2-(4-tert-butylphenoxymethyl)mandelonitrile,
2-(2,4-dimethylphenoxymethyl)mandelonitrile,
2-(2,5-dimethylphenoxymethyl)mandelonitrile,
2-(2,6-dimethylphenoxymethyl)mandelonitrile,
2-(3,5-dimethylphenoxymethyl)mandelonitrile,
2-(2,4-diethylphenoxymethyl)mandelonitrile,
2-(2,5-diethylphenoxymethyl)mandelonitrile,
2-(2,6-diethylphenoxymethyl)mandelonitrile,
2-(2,5-diisopropylphenoxymethyl)mandelonitrile,
2-(2,6-diisopropylphenoxymethyl)mandelonitrile,
2-(2,4,5-trimethylphenoxymethyl)mandelonitrile,
2-(2,4,6-trimethylphenoxymethyl)mandelonitrile,
2-(3,4,5-trimethylphenoxymethyl)mandelonitrile,
2-(2,5-dimethylphenoxymethyl)-3-chloromandelonitrile,
2-(2-methylphenoxymethyl)-3-chloromandelonitrile,
2-(2,5-dimethylphenoxymethyl)-4-chloromandelonitrile,
2-(2-methylphenoxymethyl)-4-chloromandelonitrile,
2-(2,5-dimethylphenoxymethyl)-5-chloromandelonitrile,
2-(2-methylphenoxymethyl)-5-chloromandelonitrile,
2-(2,5-dimethylphenoxymethyl)-6-chloromandelonitrile,
2-(2-methylphenoxymethyl)-6-chloromandelonitrile,
2-(2,5-diethylphenoxymethyl)-4-chloromandelonitrile,
2-(2-ethylphenoxymethyl)-4-chloromandelonitrile,
2-(2,5-diisopropylphenoxymethyl)-4-chloromandelonitrile, and
2-(2-isopropylphenoxymethyl)-4-chloromandelonitrile.

Among these compounds, 2-(2-methylphenoxymethyl) mandelonitrile and 2-(2,5-dimethylphenoxymethyl) mandelonitrile are preferred, and 2-(2,5-dimethylphenoxymethyl)mandelonitrile is more preferred.

The mandelonitrile compound (6) can be produced by reacting a corresponding aldehyde compound with hydrogen cyanide.

Examples of the alcohol compound (7) include methanol, ethanol, 1-propanol, 2-propanol, 1-butanol, and 2-butanol, and methanol is preferred.

Examples of the acid include sulfuric acid, hydrogen chloride and p-toluenesulfonic acid, and hydrogen chloride is preferred. The amount of the acid used is usually from 1 to 10 mol, and preferably from 1 to 5 mol, based on 1 mol of the mandelonitrile compound (6). Such an acid may be used by mixing with the alcohol compound (7). In particular, it is preferred to use a solution obtained by dissolving hydrogen chloride in the alcohol compound (7). The content of the hydrogen chloride in the solution obtained by dissolving the hydrogen chloride in the alcohol compound (7) is preferably from 20 to 60 parts by weight, and more preferably from 40 to 55 parts by weight, based on 100 parts by weight of the solution. When hydrogen chloride is used as the acid, the amount of the hydrogen chloride used is preferably from 1 to 5 mol, more preferably from 1.2 to 3 mol, and particularly preferably from 1.2 to 2.5 mol, based on 1 mol of the mandelonitrile compound (6).

The reaction of the mandelonitrile compound (6), the alcohol compound (7) and the acid is usually carried out in the presence of an organic solvent. Examples of the organic solvent include aromatic hydrocarbon solvents such as benzene, toluene, xylene and chlorobenzene; aliphatic hydrocarbon solvents such as hexane and heptane; alicyclic hydrocarbon solvents such as cyclopentane and cyclohexane; ketone solvents such as methyl ethyl ketone and methyl isobutyl ketone; and ether solvents such as diethylether, dibutylether, tetrahydrofuran and tetrahydropyran. These solvents may be used alone, or two or more kinds of solvents may be used in combination. Among these solvents, aromatic hydrocarbon solvents are preferred. The amount of the organic solvent used is usually from 0.5 to 10 parts by weight, and preferably from 1 to 5 parts by weight, based on 1 part by weight of the mandelonitrile compound (6).

The reaction of the mandelonitrile compound (6), the alcohol (7) and the acid is usually carried out by mixing these three components in the presence of an organic solvent, and it is preferable to add a mixture of the acid and the alcohol compound (7) to a mixture of the organic solvent and the mandelonitrile compound (6). The acid may be added at a time, and is preferably added gradually over 0.5 to 20 hours, and more preferably over 1 to 10 hours.

The reaction temperature is usually from −20 to 50° C., and preferably from 0 to 30° C. The reaction time depends on the reaction temperature, and is usually from 0.5 to 20 hours, and preferably from 1 to 10 hours.

The progress of the reaction can be recognized by general analytical means such as high-performance liquid chromatography and gas chromatography.

The reaction mixture thus obtained contains an imino ester compound represented by formula (8) or a salt thereof (hereinafter abbreviated to an imino ester compound (8)):

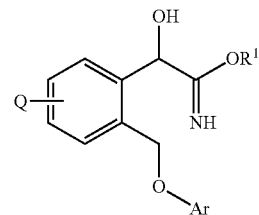

(8)

wherein Q, R¹ and Ar have the same meanings as defined above. The acetic acid ester compound (4) can be obtained by reacting the imino ester compound (8) with water. The imino ester compound (8) may be separated from the reaction mixture and reacted with water, and it is preferable to react the reaction mixture as it is with water.

The amount of water used is usually from 0.1 to 10 parts by weight, preferably from 0.5 to 5 parts by weight, and more preferably from 0.5 to 3 parts by weight, based on 1 part by weight of the mandelonitrile compound (6).

The reaction of the imino ester compound (8) with water is usually carried out by mixing both components, and there is no particular limitation on the mixing order. It is preferable to carry out the reaction by gradually adding water to a reaction mixture. The time of water added is usually from 0.5 to 20 hours, and preferably from 1 to 10 hours.

The reaction temperature is usually 0 to 70° C., and preferably 5 to 60° C. The reaction time depends on the reaction temperature, and is usually from 0.5 to 20 hours, and preferably from 1 to 10 hours.

The progress of the reaction can be recognized by general analytical means such as high-performance liquid chromatography and gas chromatography.

After completion of the reaction, the obtained reaction mixture containing the acetic acid ester compound (4) may be used in the above reaction of the acetic acid ester compound (4) with the amine compound (5) directly or after washing. Alternatively, the acetic acid ester compound (4) may be separated from the reaction mixture by concentration, crystallization or the like to use in the above reaction of the acetic acid ester compound (4) with the amine compound (5). The acetic acid ester compound (4) thus separated may be further purified by general purification means such as column chromatography.

Also, the acetamide compound (2) wherein $R^2$ is a hydrogen atom can be produced by reacting the mandelonitrile compound (6) with 0.1 to 1 mol of hydrogen chloride and 1 to 4 mol of water, based on 1 mol of the mandelonitrile compound (6). In the reaction, the formation of a carboxylic acid compound produced by the hydrolysis of the acetamide compound (2) tends to be suppressed, and thus it is a preferred method for producing the acetamide compound (2) wherein $R^2$ is a hydrogen atom.

Hydrochloric acid, an aqueous solution of hydrogen chloride, may be used instead of hydrogen chloride. When hydrochloric acid is used, the concentration of hydrogen chloride is usually from 10 to 36% by weight, and preferably from 25 to 36% by weight. As described above, the amount of hydrogen chloride used is from 0.1 to 1 mol, and preferably from 0.5 to 1 mol, based on 1 mol of the mandelonitrile compound (6). When the amount of hydrogen chloride used is 0.1 mol or more based on 1 mol of the mandelonitrile (6), the yield of the acetamide compound (2) wherein $R^2$ is a hydrogen atom tends to be improved. On the other hand, when the amount is 1 mol or less based on 1 mol of the mandelonitrile compound (6), the progress of hydrolysis reaction of the acetamide compound (2) tends to be suppressed.

Water may be used alone or simultaneously with hydrogen chloride in the form of hydrochloric acid. As described above, the amount of water used is from 1 to 4 mol, and preferably from 2 to 4 mol, based on 1 mol of the mandelonitrile compound (6). When the amount of water used is 1 mol or more based on 1 mol of the mandelonitrile compound (6), the conversion rate of the mandelonitrile compound (6) tends to be improved. On the other hand, when the amount is 4 mol or less based on 1 mol of the mandelonitrile compound (6), the progress of hydrolysis reaction of the acetamide compound (2) tends to be suppressed.

The reaction of the mandelonitrile compound (6), hydrogen chloride and water is preferably carried out in the presence of an organic solvent. Examples of the organic solvent include aromatic hydrocarbon solvents such as benzene, toluene, xylene and chlorobenzene; aliphatic hydrocarbon solvents such as hexane and heptane; alicyclic hydrocarbon solvents such as cyclopentane and cyclohexane; ketone solvents such as methyl ethyl ketone and methyl isobutyl ketone; and ether solvents such as diethyl ether, dibutyl ether, tetrahydrofuran and tetrahydropyran. These solvents may be used alone, or two or more kinds of solvents may be used in combination. Among these solvents, aromatic hydrocarbon solvents are preferred.

The amount of the organic solvent used is usually from 0.5 to 10 parts by weight, and preferably from 1 to 5 parts by weight, based on 1 part by weight of the mandelonitrile compound (6).

The reaction is carried out by mixing the mandelonitrile compound (6), hydrogen chloride and water. For example, hydrogen chloride and water may be added to the mandelonitrile compound (6), or the mandelonitrile compound (4) may be added to hydrogen chloride and water. Alternatively, the mandelonitrile compound (6) may be diluted with an organic solvent before the diluted solution is mixed with hydrogen chloride and water.

The reaction temperature is usually from −20 to 100° C., and preferably from 20 to 80° C. The reaction time depends on the reaction temperature, and is usually from 0.5 to 20 hours, and preferably from 1 to 10 hours.

The progress of the reaction can be recognized by general analytical means such as high-performance liquid chromatography and gas chromatography.

The obtained reaction mixture may be used in the above reaction of the acetamide compound (2) with the dialkyl sulfate (3) directly or after washing. Alternatively, the acetamide compound (2) may be separated from the reaction mixture by concentration, crystallization or the like, and the acetamide compound (2) separated may be used in the above reaction of the acetamide compound (2) with the dialkyl sulfate (3). The acetamide compound (2) thus separated may be further purified by general purification means such as column chromatography.

EXAMPLES

The present invention will be described in more detail below by way of Examples, but the invention is not limited thereto. The analysis was carried out using high-performance liquid chromatography according to an internal standard method.

Example 1

To 10.0 g of 2-(2,5-dimethylphenoxymethyl)-mandelonitrile (content: 96% by weight), 30 g of xylene, 3.66 g of hydrogen chloride and 0.648 g of water were added. The obtained mixture was heated to 50° C., stirred and maintained at the same temperature for 3 hours to obtain a xylene solution containing 2-[2-(2,5-dimethylphenoxymethyl)phenyl]-2-hydroxyacetamide (yield: 65.7%). The formation of by-products generated by the hydrolysis of 2-[2-(2,5-dimethylphenoxymethyl)phenyl]-2-hydroxyacetamide was not recognized.

Example 2

A xylene solution containing 2-[2-(2,5-dimethylphenoxymethyl)phenyl]-2-hydroxyacetamide was obtained by carrying out the reaction in the same manner as in Example 1, except that the obtained mixture was heated to 70° C., stirred and maintained at the same temperature for 1 hour in Example 1. The conversion rate of 2-(2,5-dimethylphenoxymethyl) mandelonitrile was 67.7%, and the yield of 2-[2-(2,5-dimethylphenoxymethyl)phenyl]-2-hydroxyacetic acid amide was 46.3%. The formation of by-products generated by the hydrolysis of 2-[2-(2,5-dimethylphenoxymethyl)phenyl]-2-hydroxyacetamide was not recognized.

Example 3

To 10.0 g of 2-(2,5-dimethylphenoxymethyl)-mandelonitrile (content: 96% by weight), 30 g of xylene and 1.02 g of 36% by weight hydrochloric acid were added. The obtained mixture was heated to 50° C., stirred and maintained at the same temperature for 7 hours to obtain a reaction mixture containing 2-[2-(2,5-dimethylphenoxymethyl)phenyl]-2-hydroxyacetamide. The conversion rate of 2-(2,5-dimethylphenoxymethyl)mandelonitrile was 40.0%, and the yield of 2-[2-(2,5-dimethylphenoxymethyl)phenyl]-2-hydroxyacetamide was 30.2%. The formation of by-products generated by the hydrolysis of 2-[2-(2,5-dimethylphenoxymethyl)phenyl]-2-hydroxyacetamide was not recognized.

Example 4

A reaction mixture containing 2-[2-(2,5-dimethylphenoxymethyl)phenyl]-2-hydroxyacetamide was obtained by carrying out the reaction in the same manner as in Example 3, except that the amount of 36% hydrochloric acid used was 2.03 g and the obtained mixture was stirred and maintained at 50° C. for 4 hours in Example 3. The conversion rate of 2-(2,5-dimethylphenoxymethyl)mandelonitrile was 68.4%, and the yield of 2-[2-(2,5-dimethylphenoxymethyl)phenyl]-2-hydroxyacetamide was 53.1%. The formation of by-products generated by the hydrolysis of 2-[2-(2,5-dimethylphenoxymethyl)phenyl]-2-hydroxyacetamide was not recognized.

Example 5

A xylene solution containing 0.33 g of 2-[2-(2,5-dimethylphenoxymethyl)phenyl]-2-hydroxyacetamide was adjusted to 20° C. with stirring. To the xylene solution, 1.2 g of a 48% by weight aqueous sodium hydroxide solution was added dropwise over 1 hour, followed by 0.70 g of dimethyl sulfate over 1 hour. The obtained mixture was stirred at 20° C. for 5 hours to obtain a reaction mixture containing 2-[2-(2,5-dimethylphenoxymethyl)phenyl]-2-methoxy-N-methylacetamide.

To the obtained reaction mixture, 1.3 g of water was added. The obtained mixture was heated to 50° C., and the water layer was then removed. The obtained organic layer was washed at 50° C. with 1.3 g of 5% by weight hydrochloric acid. The obtained organic layer was washed at 50° C. with 1.3 g of water. The obtained organic layer was concentrated to obtain 0.36 g (content: 96.5%) of 2-[2-(2,5-dimethylphenoxymethyl)phenyl]-2-methoxy-N-methylacetamide (yield: 96%). The formation of 2-[2-(2,5-dimethylphenoxymethyl)phenyl]-2-methoxy-N,N'-dimethylacetamide was not recognized.

Example 6

First, 255.9 g (content: 93% by weight) of 2-(2,5-dimethylphenoxymethyl)mandelonitrile was mixed with 469.0 g of xylene. The obtained mixture was adjusted to 7° C. with stirring. To the mixture, 160.1 g of a 47% by weight hydrogen chloride/methanol solution was added dropwise over 2 hours. The obtained mixture was stirred and maintained at 7° C. for 2 hours to obtain a reaction mixture containing 1-[2-(2,5-dimethylphenoxymethyl)phenyl]-1-hydroxy-2-methoxyethaneiminium chloride.

To the obtained reaction mixture, 320.1 g of water was added dropwise at 7° C. over 1 hour. The obtained mixture was stirred and maintained at 50° C. for 1 hour, and 312.6 g of an organic layer was then separated. The content of methyl 2-[2-(2,5-dimethylphenoxymethyl)phenyl]-2-hydroxyacetate in the organic layer was 82.4% by weight, and the yield was 96.2%.

Example 7

Then, 30.0 g (content: 25% by weight) of the organic layer containing methyl 2-[2-(2,5-dimethylphenoxymethyl)phenyl]-2-hydroxyacetate was adjusted to 50° C. with stirring. To the layer, 5.8 g of a 40% by weight methylamine/methanol solution was added dropwise over 1 hour. The obtained mixture was stirred and maintained at 50° C. for 10 hours to obtain a reaction mixture containing 2-[2-(2,5-dimethylphenoxymethyl)phenyl]-2-hydroxy-N-methylacetamide.

The obtained reaction mixture was concentrated under reduced pressure conditions to remove low-boiling components. The residue was adjusted to 50° C., and washed with 7.7 g of water and then with 7.7 g of a 5% by weight aqueous sulfuric acid solution to obtain 31.5 g of a solution (content: 23.8% by weight) containing 2-[2-(2,5-dimethylphenoxymethyl)phenyl]-2-hydroxy-N-methylacetamide. Yield: 100%.

Example 8

Then, 31.1 g of the solution containing 2-[2-(2,5-dimethylphenoxymethyl)phenyl]-2-hydroxy-N-methylacetamide obtained in Example 7 was adjusted to 17° C. with stirring. To the solution, 7.0 g of a 48% by weight aqueous sodium hydroxide solution was added dropwise over 0.5 hour, followed by 4.2 g of dimethyl sulfate over 2 hours. The obtained mixture was stirred and maintained at 19° C. for 5 hours to obtain a reaction mixture containing 2-[2-(2,5-dimethylphenoxymethyl)phenyl]-2-methoxy-N-methylacetamide.

To the obtained reaction mixture, 7.4 g of water was added. The obtained mixture was heated to 50° C., and an organic layer was obtained at the same temperature. The obtained organic layer was washed at the same temperature with 7.4 g of 5% by weight hydrochloric acid and then with 7.5 g of water to obtain 32.1 g of a solution (content: 24.0% by weight) containing 2-[2-(2,5-dimethylphenoxymethyl)phenyl]-2-methoxy-N-methylacetamide. Yield: 99.1%.

The obtained solution was concentrated until the content of 2-[2-(2,5-dimethylphenoxymethyl)phenyl]-2-methoxy-N-methylacetamide was 42.5% by weight, and then heated to 60° C. The obtained solution was cooled, and crystals precipitated were separated by filtration, washed with heptane, and dried under reduced pressure conditions to obtain crystals of 2-[2-(2,5-dimethylphenoxymethyl)phenyl]-2-methoxy-N-methylacetamide.

INDUSTRIAL APPLICABILITY

According to the present invention, a phenylacetamide compound can be produced in a satisfactory yield.

The invention claimed is:
1. A method for producing a phenylacetamide compound represented by formula (1):

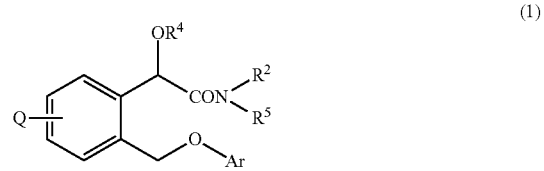

wherein Q represents a hydrogen atom or a halogen atom, $R^2$ represents a hydrogen atom or an alkyl group having 1 to 4 carbon atoms, $R^4$ represents an alkyl group having 1 to 4 carbon atoms, Ar represents an unsubstituted or substituted phenyl group, $R^5$ represents $R^4$ when $R^2$ is a hydrogen atom, and $R^5$ represents a hydrogen atom when $R^2$ is an alkyl group having 1 to 4 carbon atoms; comprising reacting a phenylacetamide compound represented by formula (2):

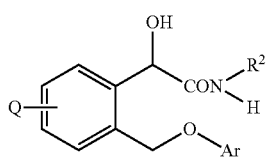

(2)

wherein Q, $R^2$ and Ar have the same meanings as defined above;

with a dialkyl sulfate represented by formula (3):

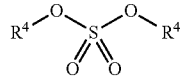

(3)

wherein $R^4$ has the same meaning as defined above;

in the presence of a base.

2. The production method according to claim 1, wherein $R^2$ is a hydrogen atom.

3. The production method according to claim 1, wherein Ar is a 2,5-dimethylphenyl group or a 2-methylphenyl group.

4. The production method according to claim 1, wherein Ar is a 2,5-dimethylphenyl group.

5. The production method according to claim 1, wherein $R^4$ is a methyl group.

6. The production method according to claim 1, wherein the base is an alkali metal hydroxide.

7. The production method according to claim 1, wherein the phenylacetamide compound represented by formula (2) is a phenylacetamide compound obtained by reacting an acetic acid ester compound represented by formula (4):

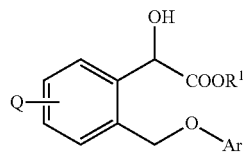

(4)

wherein Q represents a hydrogen atom or a halogen atom, Ar represents an unsubstituted or substituted phenyl group, and $R^1$ represents an alkyl group having 1 to 4 carbon atoms;

with an amine compound represented by formula (5):

  $R^2$—$NH_2$ (5)

wherein $R^2$ represents a hydrogen atom or an alkyl group having 1 to 4 carbon atoms.

8. The production method according to claim 7, wherein the reaction of the acetic acid ester compound represented by formula (4) with the amine compound represented by formula (5) is carried out in the presence of an alcohol solvent having 1 to 4 carbon atoms.

9. The production method according to claim 7, wherein the acetic acid ester compound represented by formula (4) is an acetic acid ester compound obtained by reacting a mandelonitrile compound represented by formula (6):

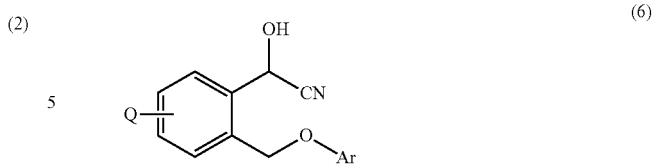

(6)

wherein Q represents a hydrogen atom or a halogen atom, and Ar represents an unsubstituted or substituted phenyl group;

with an alcohol compound represented by formula (7):

  R—OH (7)

wherein $R^1$ represents an alkyl group having 1 to 4 carbon atoms;

and an acid, and then reacting the resulting product with water.

10. The production method according to claim 2, wherein the phenylacetamide compound represented by formula (2) is a phenylacetamide compound obtained by reacting a mandelonitrile compound represented by formula (6):

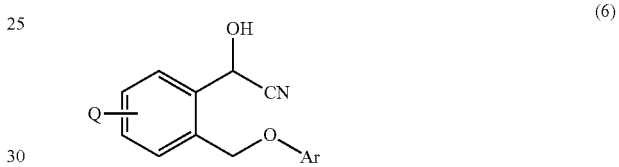

(6)

wherein Q represents a hydrogen atom or a halogen atom, and Ar represents an unsubstituted or substituted phenyl group;

with 0.1 to 1 mol of hydrogen chloride and 1 to 4 mol of water, based on 1 mol of the mandelonitrile compound represented by formula (6).

11. The production method according to claim 10, wherein the reaction of the mandelonitrile compound represented by formula (6) with hydrogen chloride and water is carried out in the presence of an aromatic hydrocarbon solvent.

12. A method for producing a phenylacetamide compound represented by formula (8):

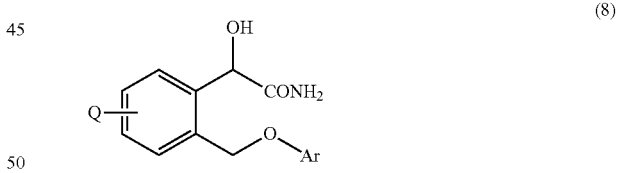

(8)

wherein Q represents a hydrogen atom or a halogen atom, and Ar represents an unsubstituted or substituted phenyl group;

comprising reacting a mandelonitrile compound represented by formula (6):

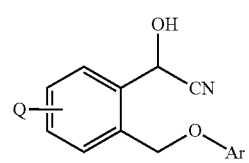

(6)

wherein Q and Ar have the same meanings as defined above;

with 0.1 to 1 mol of hydrogen chloride and 1 to 4 mol of water, based on 1 mol of the mandelonitrile compound represented by formula (6).

13. The production method according to claim 12, wherein the reaction of the mandelonitrile compound represented by formula (6) with hydrogen chloride and water is carried out in the presence of an aromatic hydrocarbon solvent.

* * * * *